United States Patent
Karlsson

[11] Patent Number: 5,741,284
[45] Date of Patent: Apr. 21, 1998

[54] DIALYSIS COMBINATION AND MICRODIALYSIS PROBE AND INSERTION DEVICE

[75] Inventor: Hans Karlsson, Sollentuna, Sweden

[73] Assignee: CMA/Microdialysis Holding AB, Solna, Sweden

[21] Appl. No.: 682,745

[22] PCT Filed: Feb. 1, 1995

[86] PCT No.: PCT/SE95/00096

§ 371 Date: Jul. 31, 1996

§ 102(e) Date: Jul. 31, 1996

[87] PCT Pub. No.: WO95/20991

PCT Pub. Date: Aug. 10, 1995

[30] Foreign Application Priority Data

Feb. 4, 1994 [SE] Sweden .................... 9400378

[51] Int. Cl.⁶ .................... A61M 5/178
[52] U.S. Cl. .................... 604/160; 604/158; 604/161
[58] Field of Search .................... 604/160, 158, 604/161, 171, 177, 167, 27, 29

[56] References Cited

U.S. PATENT DOCUMENTS

| | | | |
|---|---|---|---|
| 3,359,978 | 12/1967 | Smith | 604/161 |
| 3,472,232 | 10/1969 | Earl | 604/160 |
| 3,584,625 | 6/1971 | Swick | 604/161 |
| 3,603,311 | 9/1971 | Huggins | 604/161 |
| 3,827,434 | 8/1974 | Thompson et al. | |
| 4,354,491 | 10/1982 | Marbry | |
| 4,377,165 | 3/1983 | Luther | 604/160 |
| 5,106,365 | 4/1992 | Hernandez | 604/27 |
| 5,441,481 | 8/1995 | Mishra | 604/29 |

FOREIGN PATENT DOCUMENTS 0 261 835  3/1988  European Pat. Off.

Primary Examiner—Sam Rimell
Assistant Examiner—Luke Yeh
Attorney, Agent, or Firm—Young & Thompson

[57] ABSTRACT

A dialysis probe combination with a microdialysis probe (1) which can be inserted into tissue with the aid of an insertion device that includes a canula tube (9). In order to be able to remove the canula tube (9) after insertion, the tube is provided with a slot along the whole of its length, this slot preferably including an angle of about 65° in the radial direction. During insertion, the probe is held within the canula tube by virtue of the major part of the probe being larger than the slot. However, the proximal portion of the probe includes a flattened part which is able to pass through the slot, and the canula tube can be drawn past the flattened part by lifting this part, while leaving the probe in the tissue.

6 Claims, 1 Drawing Sheet

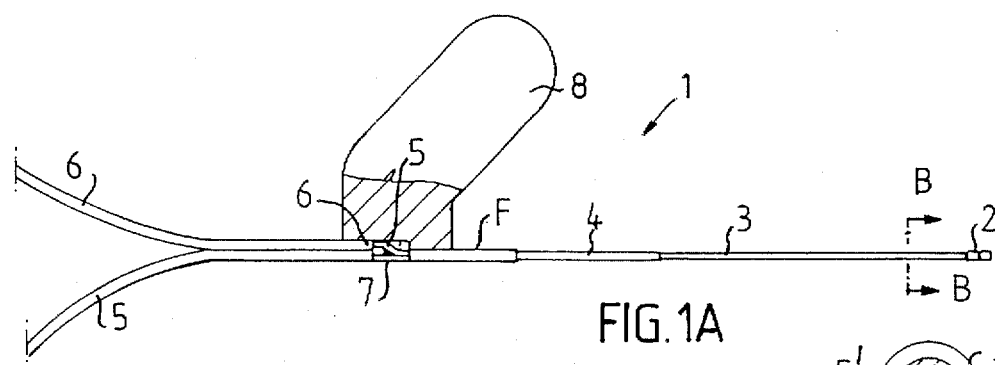
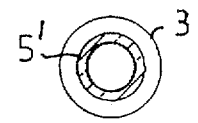
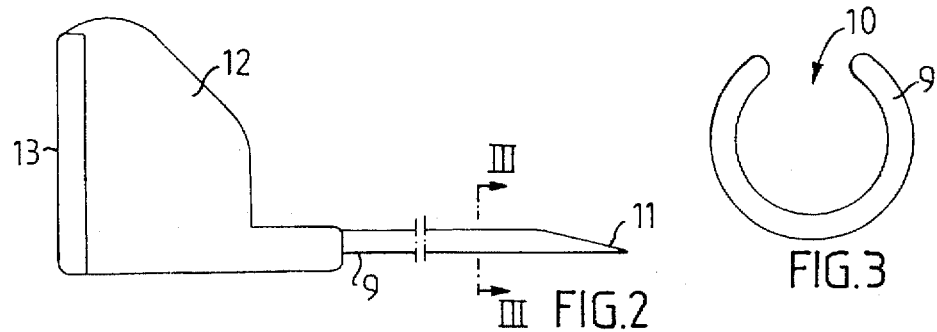
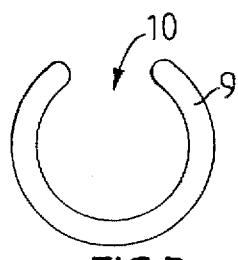
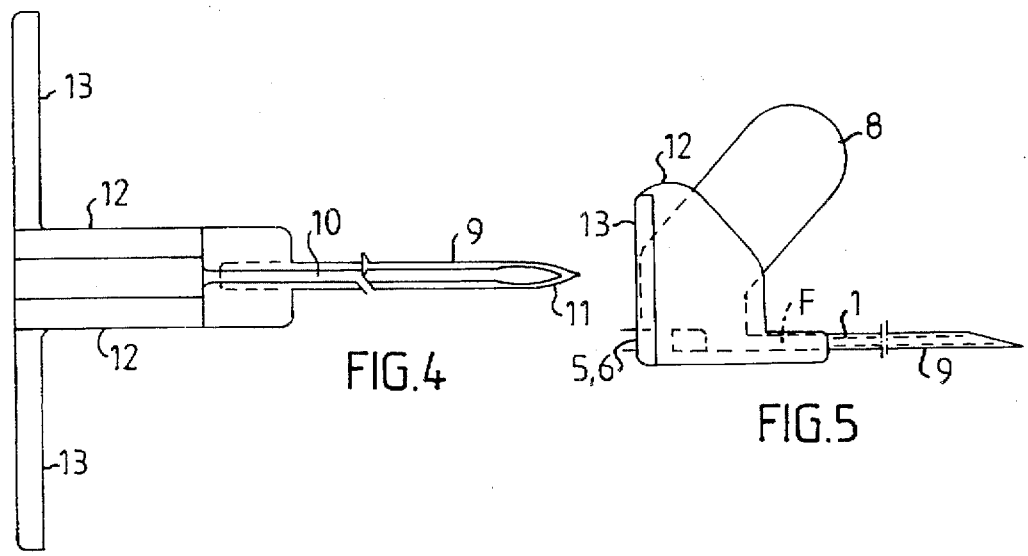

5,741,284

DIALYSIS COMBINATION AND MICRODIALYSIS PROBE AND INSERTION DEVICE

FIELD OF THE INVENTION

The invention relates to a dialysis probe combination, a microdialysis probe and an insertion device.

BACKGROUND OF THE INVENTION

By microdialysis is meant an investigatory procedure in which a probe is inserted in vivo in tissue, such that one side of a semi-permeable membrane will be in contact with tissue and body fluid, while the other side is flushed with a dialysis liquid which takes up substances through the membrane, wherewith these substances can then be analyzed in the liquid that flows past. A microdialysis probe is known from SE-C-434 214. This method has made significant advances over recent years, and the number of research publications that are connected with microdialysis have increased a thousand-fold in ten years.

The use in clinical and polyclinical activities for diagnostic purposes on human beings, however, has been retarded, primarily because dialysis probes are naturally quite fragile, which makes them difficult to insert. At least one part of the probe must have a surface which is comprised of a thin, semi-permeable membrane, which is easily broken.

U.S. Pat. No. 4,354,491 teaches single-slot canula tubes which after inserting a catheter into a vein can be withdrawn from the body, whereafter the outer part of the catheter can be withdrawn out of the slot. This patent publication also describes a canula tube which includes two mutually opposing, longitudinally extending slots of which one terminates immediately prior to the tip, and with which the two parts of the canula tube are held together at the other end by means of a separate fitting. However, neither solution can be used with a microdialysis catheter, due to the fact that it must include at its proximal end a connecting part for connection to an ingoing and an outgoing hose, this connector part being necessarily of larger diameter than the inner diameter of the canula tube. Thus, it is necessary in both cases to extend the catheter without increasing its diameter, which increases its dead volume.

It is also known to insert a plastic hose fitted on a stiffening metal canula tube having a cutting tip, this canula tube being withdrawn after insertion. A catheter can then be inserted in the hose and the hose, which can be readily torn along two generatrices, can then be withdrawn and pulled apart at weakenings provided to this end, so as to be eliminated.

In the case of the aforesaid known arrangement, which has been found usable for applying microdialysis probes, the work involved is relatively troublesome and requires the use of two hands for manoeuvering and splitting the canula tube or the hose and a further hand for preventing the microdialysis probe from accompanying the canula tube as the canula tube is withdrawn. The problems associated with insertion have therefore retarded the use of the microdialysis method for clinical and polyclinical examinations. An object of the present invention is to provide a microdialysis combination which will eliminate these difficulties and which will even make it possible for a patient or a relative to insert a microdialysis probe, something which has been unthinkable hitherto.

SUMMARY OF THE INVENTION

These and other objects and advantages are achieved in accordance with the invention with a dialysis probe combination according to the above that has the characteristic features set forth in the claims. According to the invention, a dialysis probe and a canula tube are used whose particular configuration makes the invention possible and which have the characterizing features set forth in the claims.

When applying the invention, a separate canula tube having an inwardly lying probe is inserted to the position in which the probe shall lie, possibly after having pierced the actual skin as a preparatory measure. During insertion the probe lies within the canula tube, wherewith at least the distal part of the probe and parts of its proximal part are sufficiently large to be unable to leave the canula tube through its longitudinally extending slot. When the canula tube is to be withdrawn, the probe is withdrawn through the canula tube slot at the proximal end of the canula tube, at which position the probe is narrowed or flattened so as to be able to pass through the slot. This narrowed part is held firmly adjacent the surface of the skin, whereafter the canula tube can be easily withdrawn past the narrowed part. The canula tube and the probe can be gripped in each hand, particularly when the canula tube and the probe are each provided with a suitable handgrip, thereby enabling withdrawal to be effected by one single person. A fairly handy person can even carry this out entirely alone, at least when the position is accessible to the patient. The invention therewith improves the possibility of using this method of examination clinically and polyclinically, which is highly promising with respect to the investigation of many systemic states, such as diabetes, for instance. It is also possible to deliver different substances to the body.

BRIEF DESCRIPTION OF THE DRAWINGS

The invention will now be described in more detail with reference to a non-limiting exemplifying embodiment thereof and also with reference to the accompanying drawings. FIG. 1A illustrates a microdialysis probe. FIG. 1B is a sectional view of a microdialysis probe, taken on the line B—B in FIG. 1A. FIG. 2 is a side view of an insertion device. FIG. 3 is a section view of the canula tube of the insertion device shown in FIG. 2, taken on the lines III—III. FIG. 4 shows the insertion device of FIG. 2 from above. FIG. 5 is a schematic illustration of an insertion device having a microdialysis probe inserted therein.

DETAILED DESCRIPTION OF THE INVENTION

The microdialysis probe 1 shown in FIG. 1A includes between an end part 2 and an intermediate part 4 a mantle part 3 which is semi-permeable at least at a part of its surface. As shown in FIG. 1B, a thin inner tube 5' is located within the mantle part 3 such as to form in cross-section an annular space between the inner tube 5' and the mantle part 3. Although not shown, the inner tube has an opening located close to the end part 2. The inner tube and the annular space are each connected to a respective line 5, 6 which can be connected respectively to a source of dialysis liquid and a sampler. Since these components form no part of the invention, their details will not be further described.

FIGS. 2–4 show an insertion device for the microdialysis probe shown in FIG. 1. This insertion device includes a canula tube 9 having a pointed tip 11. The canula tube 9 is fastened to a handle means 12, 13, which in the illustrated case is made of plastic. The particular feature of the canula tube 9 is that it is provided with a slot 10 best seen from the cross-sectional view of FIG. 3, which extends approximately along the full length of the canula tube. In order to provide a holding facility, the slot must occupy an angle of less than 180°, and preferably occupies an angle of about 65°.

The inner diameter of the canula tube 9 and the dimensions of the slot 10 are adapted so that the major part of the insertible portion of the microdialysis probe 1 will fit slidingly in the canula tube, while the slot 10 is too narrow to permit the probe to be removed radially. Thus, at least the end part 2 of the probe and the intermediate part 4 should be larger than the slot 10, with one exception which enables the function of the invention: The plastic hose 4 is namely flattened from one side at F, such that its essentially elliptical form at this point has a minor axis which is slightly smaller than the width of the slot. This enables the probe to be curved at F after having inserted the canula tube into tissue with the microdialysis probe inside the canula tube, such that the outer probe end will be located outside the imaginary outward extension of the bore of the canula tube 9 at the position F. When the canula tube is then withdrawn from the tissue, it can be drawn past the stationary flattening F, so as to leave the microdialysis probe in position after the canula tube has been fully withdrawn.

The aforedescribed operation is facilitated by the various handle parts shown in the Figures: The microdialysis probe has a flat wing 8 which is suitably held firmly so as to prevent the microdialysis probe 1 from being withdrawn at the same time as the canula tube. The canula tube handle part consists in two upstanding parts 12 which form a slot in the extension of the canula tube slot 10, said wing 8 fitting into the slot as will best be seen from FIG. 5. The upstanding parts carry finger-grip wings 13. This enables the canula tube to be withdrawn with the aid of two fingers of one hand hooked around the finger-grip wings 13, while the wing 8 fixedly mounted on the microdialysis probe 1 is held firmly with the other hand, in order to prevent simultaneous withdrawal of the probe. After the canula tube has been withdrawn and discarded, the wing 8 can be suitably folded down against the skin and secured thereto with adhesive tape, therewith providing certain resistance to withdrawing and bending forces in the connection lines 5 and 6.

A canula tube of this kind, provided with a slot 10, can be produced conveniently by drawing a rolled band of stainless steel around a mandril through an appropriately configured draw plate of a wire drawing kind.

The illustrated canula tube can, in many cases, be fully sufficient for inserting a canula through the skin. In other cases, when the skin is very tough, it is suitable to first pierce the skin with a lancet-like point, so that the hole through the skin will not clamp elastically around the canula tube and make insertion of the probe-fitted canula difficult.

The invention greatly facilitates the insertion of a microdialysis probe, because only two hands are required and not three, and because patients possessing normal subtle motoria will often be able to insert the probe themselves.

I claim:

1. In a dialysis probe combination comprising a microdialysis probe which includes a semi-permeable membrane located and supported between two tubular members, with an inner tube which is provided with an opening at its distal end, and an outer mantle which includes the membrane, wherein the inner tube and the space defined between the inner tube and the outer mantle are each connected to a respective connecting pipe at the proximal end of the probe, and an insertion device which includes a removable cannula tube which is pointed at its distal end and which functions to stiffen the probe, the improvement wherein the cannula tube has a slot which extends along the full length of the cannula tube, and includes at its proximal end centrally opposite the slot a slot-exposing gripping element which is provided with at least one handle means which projects laterally outwards; the outer mantle and the two tubular members are slidably accommodated within the cannula tube wherein at least the tubular members are held generally firm against lateral movement by virtue of their fit in the cannula tube; a proximal end of the probe having at least one narrow part which fits in the slot, thereby enabling the cannula with the microdialysis probe inserted therein to be inserted through the skin and into the underlying tissue, wherein after insertion the narrowed probe part can be withdrawn through the slot in the cannula tube at the proximal end of said slot when the probe is located outside the skin, whereafter the complete cannula tube can be withdrawn with the slot passing beyond the stationary narrow part of the probe.

2. A dialysis probe combination according to claim 1, wherein attached to the proximal end of the probe is a gripping element which can be brought to a position opposite the slot in the cannula tube so as to bring the narrow part into the slot and so as to hold the probe firmly as the cannula tube is withdrawn past the probe.

3. A microdialysis probe comprising: a semi-permeable membrane located between two tubular members having an inner tube which is provided with an opening at its distal end, and an outer mantle which includes the membrane, wherein the inner tube and an space defined between the inner tube and the outer mantle are each connected to a respective connecting pipe at the proximal end of a probe, and the probe has close to its proximal end at least one flattened part which narrows at sides thereof.

4. A probe according to claim 3, wherein a single-directional flat handle, which coincides essentially to a plane of said flattened part is attached to said probe proximate said flattened part.

5. An insertion device for inserting a tubular microdialysis probe into tissue, comprising:

a cannula tube which has a point at its distal end;

an axial slot which extends along the full length of the cannula tube, wherein the slot has a radial angle of approximately 65°; and a handle attached to a proximal end of the cannula tube, said handle comprising two adjacent walls that are affixed to the proximal end on opposite sides of the slot, each of said walls having a surface which is parallel to and faces a corresponding said surface of the other of said walls, said facing surfaces having a zone therebetween in the radial extension of the axial slot which is wider than the slot, each of said walls having affixed thereto a finger-grip wing which extends outwardly at a right angle.

6. An insertion device for inserting a tubular microdialysis probe into tissue, comprising:

a cannula tube which has a circumferential wall of even thickness and a point at its distal end;

an axial slot which extends along the full length of the cannula tube and which has longitudinal edges which define the circumferential extent of said wall of even thickness, wherein the slot has a radial angle of less than 180°; and a handle attached to a proximal end of the cannula tube, said handle having two parallel walls, each with a surface that faces a corresponding said surface on the other of said two parallel walls, said two parallel walls being affixed to the proximal end on opposite sides of the slot and having a zone between their facing surfaces in the radial extension of the axial slot which is wider than the slot, each of said two parallel walls having affixed thereto a finger-grip wing which extends outwardly at a right angle.

* * * * *